United States Patent
Alexander et al.

(10) Patent No.: US 11,268,940 B2
(45) Date of Patent: Mar. 8, 2022

(54) HAZARDOUS GAS DETECTOR WITH 1D ARRAY CAMERA

(71) Applicant: Carrier Corporation, Jupiter, FL (US)

(72) Inventors: Jennifer M. Alexander, Roseville, MN (US); Michael J. Birnkrant, Wethersfield, CT (US); Jose-Rodrigo Castillo-Garza, West Hartford, CT (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 245 days.

(21) Appl. No.: 16/623,523

(22) PCT Filed: May 23, 2018

(86) PCT No.: PCT/US2018/034105
§ 371 (c)(1),
(2) Date: Dec. 17, 2019

(87) PCT Pub. No.: WO2018/236530
PCT Pub. Date: Dec. 27, 2018

(65) Prior Publication Data
US 2021/0148873 A1  May 20, 2021

Related U.S. Application Data

(60) Provisional application No. 62/523,023, filed on Jun. 21, 2017.

(51) Int. Cl.
*G01N 33/00* (2006.01)
*G01J 5/00* (2006.01)
*H04N 5/33* (2006.01)

(52) U.S. Cl.
CPC .......... *G01N 33/004* (2013.01); *G01J 5/0014* (2013.01); *H04N 5/33* (2013.01); *G01J 2005/0077* (2013.01)

(58) Field of Classification Search
CPC .................. G01N 33/004; G01J 5/0014; G01J 2005/0077; G01J 2003/423; G01J 3/42;
(Continued)

(56) References Cited

U.S. PATENT DOCUMENTS

2002/0071122 A1   6/2002   Kulp et al.
2006/0203248 A1   9/2006   Reichardt et al.
(Continued)

FOREIGN PATENT DOCUMENTS

CN   104730539 A   6/2015
EP   0287929 A2    10/1988
(Continued)

OTHER PUBLICATIONS

Edgar, Matthew P., et al., "Simultaneous real-time visible and infrared video with single-pixel detectors", Nature.com, Scientific Reports, published May 22, 2015, 8 pages.
(Continued)

*Primary Examiner* — David P Porta
*Assistant Examiner* — Meenakshi S Sahu
(74) *Attorney, Agent, or Firm* — Cantor Colburn LLP

(57) ABSTRACT

A hazardous gas detector that includes a housing defining an interior region is provided. Also included is a laser emitting component oriented to emit a laser light away from the housing. Further included is a lens disposed within an aperture defined by the housing, the lens allowing returning infrared light of the laser light to enter the interior region.

(Continued)

Yet further included is a mirror disposed within the interior region and oriented to split the returning laser light into a short wave infrared light and a long wave infrared light. Also included is a one-dimensional (1D) camera pixel array disposed within the interior region, the 1D camera imaging a planar region that includes an illuminated portion comprising the short wave infrared light.

18 Claims, 4 Drawing Sheets

(58) Field of Classification Search
CPC ........ G01J 3/0227; G01J 3/021; G01J 3/2803; H04N 5/33
See application file for complete search history.

(56) References Cited

U.S. PATENT DOCUMENTS

| | | |
|---|---|---|
| 2011/0102565 A1 | 5/2011 | Wang et al. |
| 2011/0181879 A1 | 7/2011 | Chen et al. |
| 2012/0176600 A1 | 7/2012 | Falk et al. |
| 2014/0183362 A1 | 7/2014 | Islam |
| 2014/0198315 A1 | 7/2014 | Priore et al. |
| 2014/0312161 A1 | 10/2014 | Ell |
| 2015/0309262 A1 | 10/2015 | Hansen |
| 2016/0267669 A1 | 9/2016 | Justice et al. |
| 2016/0349228 A1* | 12/2016 | Kester ........................ G01J 3/36 |
| 2017/0089829 A1* | 3/2017 | Bartholomew ......... G01S 17/86 |

FOREIGN PATENT DOCUMENTS

| | | |
|---|---|---|
| EP | 1602918 B1 | 1/2016 |
| EP | 3040706 A1 | 7/2016 |
| FR | 2704651 A1 | 11/1994 |
| WO | 2014143276 A2 | 9/2014 |

OTHER PUBLICATIONS

Gibson, Graham M., et al., "Real-time imaging of methane gas leaks using a single-pixel camera", Optics Express, vol. 25, No. 4, Feb. 20, 2017, 8 pages.

International Search Report and Written Opinion for application PCT/US2018/034105, dated Sep. 14, 2018, U301260UPCT, 24 pages.

Princeton Infrared Technologies, "1024L1 Linear Array", available at: https://www.princetonirtech.com/products/1024l1-linear-array, 2017, 6 pages.

Sun, B. et al., "3D Computational Imaging with Single-Pixel Detectors", available at: http://www.glasgowheart.org/media/media_278494_en.pdf , Science Magazine, May 17, 2013, 4 pages.

* cited by examiner

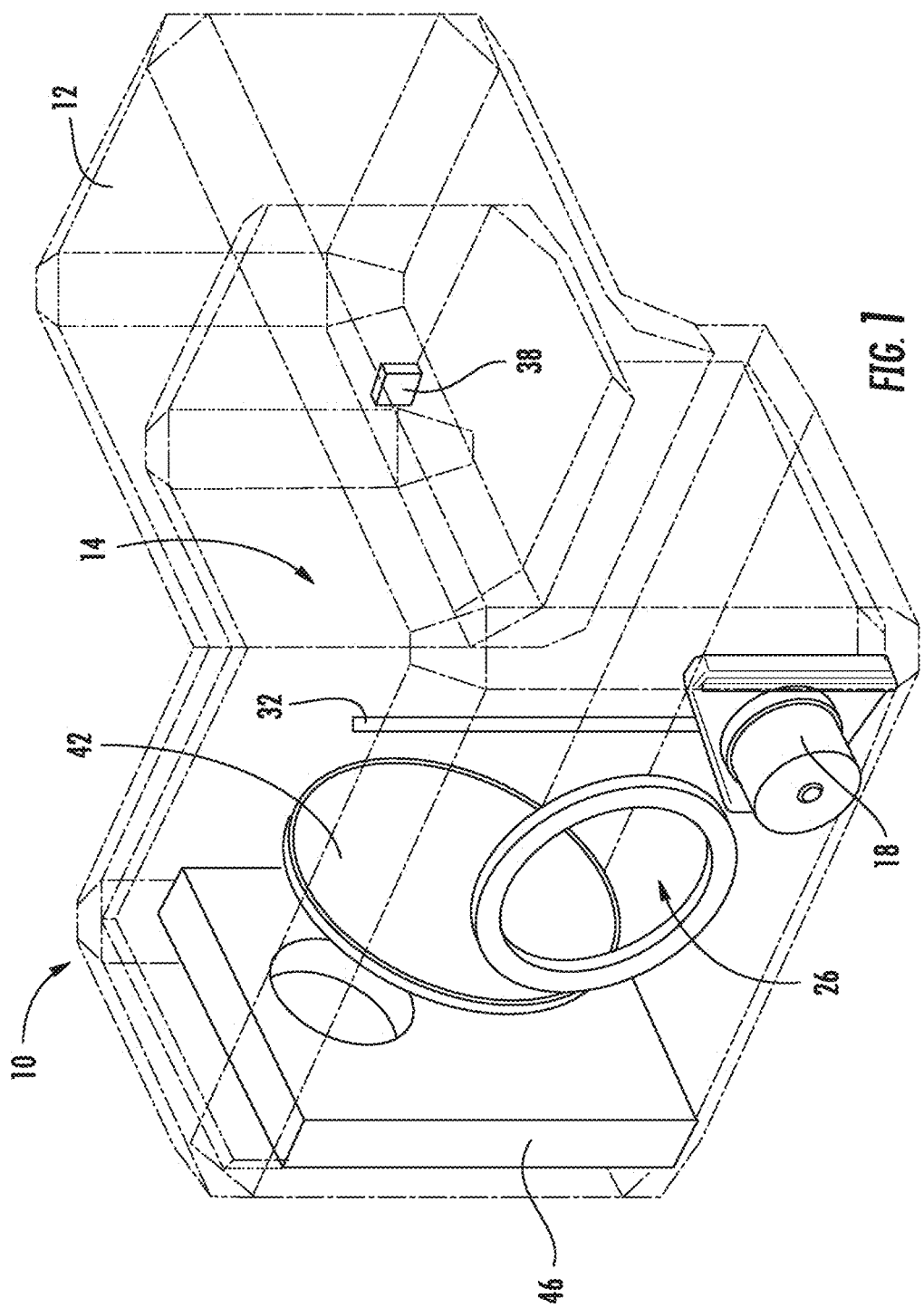

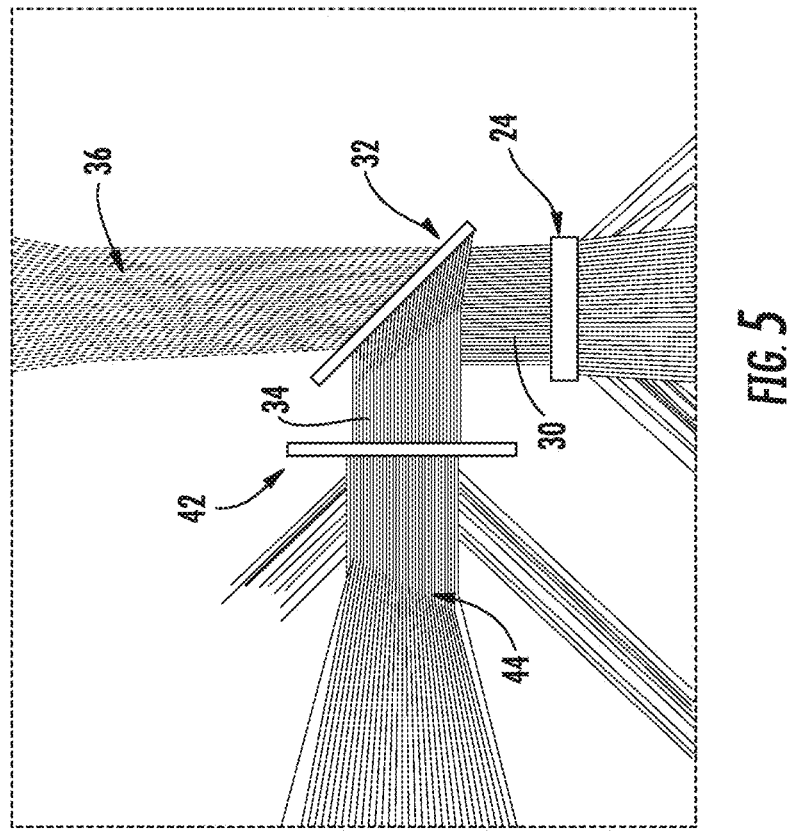
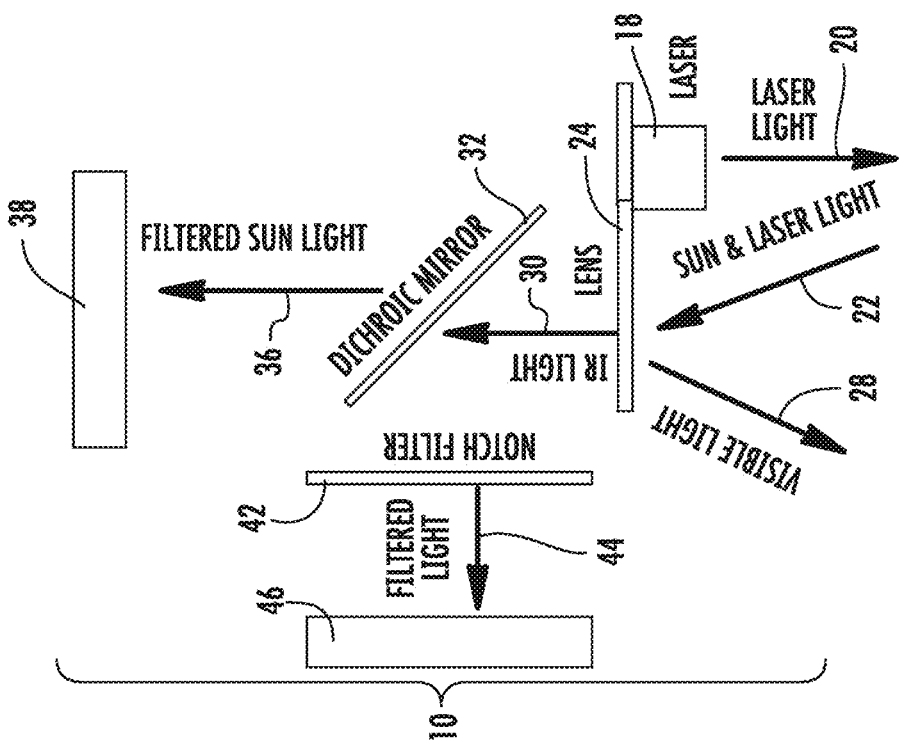
FIG. 5
FIG. 4

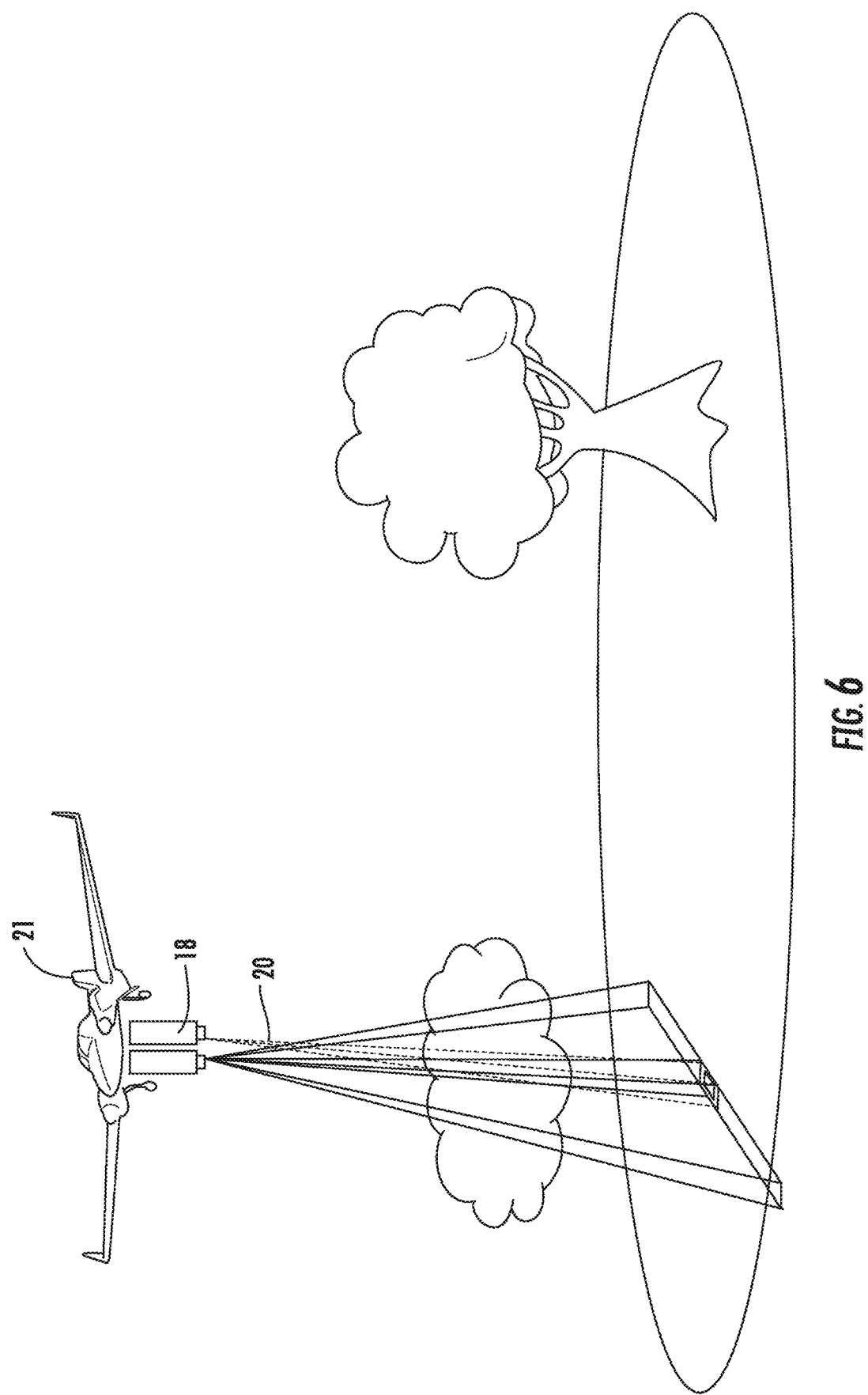

HAZARDOUS GAS DETECTOR WITH 1D ARRAY CAMERA

BACKGROUND

Exemplary embodiments pertain to hazardous gas detectors.

Hazardous gas detectors typically utilize electrochemical cells, 2D array cameras, or Light Detection and Ranging (LIDAR) components. Electrochemical cells enable fast and cheap point detection, but are prone to false alarms. 2D arrays enable wide area detection, but they tend to be prone to false alarms and export compliant. LIDAR is advantageous because it is cost effective, but requires sophisticated models, which reduces system accuracy. Therefore, an accurate hazardous gas detector that combines the advantages of 2D arrays and LIDAR would have lower false alarm rates and be export compliant.

BRIEF SUMMARY

Disclosed is a hazardous gas detector including a housing defining an interior region. Also included is a laser emitting component oriented to emit a laser light away from the housing. Further included is a lens disposed within an aperture defined by the housing, the lens allowing returning infrared light of the laser light to enter the interior region. Yet further included is a mirror disposed within the interior region and oriented to split the returning laser light into a short wave infrared light and a long wave infrared light. Also included is a one-dimensional (1D) camera pixel array disposed within the interior region, the 1D camera imaging a planar region that includes an illuminated portion comprising the short wave infrared light.

In addition to one or more of the features described above, or as an alternative, further embodiments may include that a plurality of images captured with the 1D camera determines a quantity of a gas present in an environment surrounding the housing based on an amount of absorption of the laser light emitted from the housing.

In addition to one or more of the features described above, or as an alternative, further embodiments may include that the gas comprises carbon monoxide or methane.

In addition to one or more of the features described above, or as an alternative, further embodiments may include at least one optical notch filter disposed within the housing and between the mirror and the 1D camera pixel array.

In addition to one or more of the features described above, or as an alternative, further embodiments may include that the 1D camera pixel array is a 1D short wave infrared focal plane array.

In addition to one or more of the features described above, or as an alternative, further embodiments may include that the 1D camera pixel array comprises a number of pixels ranging from 128 to 1028.

In addition to one or more of the features described above, or as an alternative, further embodiments may include a two-dimensional (2D) camera disposed within the housing for imaging of the long wave infrared light.

In addition to one or more of the features described above, or as an alternative, further embodiments may include that the 2D camera is a 2D long wave infrared focal plane array.

In addition to one or more of the features described above, or as an alternative, further embodiments may include that the 2D camera provides an image for visual inspection by a user.

In addition to one or more of the features described above, or as an alternative, further embodiments may include that the mirror is a dichroic mirror.

In addition to one or more of the features described above, or as an alternative, further embodiments may include that the housing is operatively coupled to a gimbal mount to allow movement of the housing.

Also disclosed is a method of detecting hazardous gas. The method includes emitting a laser light from a housing. Also included is receiving an infrared light portion of the laser light through a lens disposed within an aperture defined by the housing. Further included is separating a short wave infrared light from the infrared light portion with a dichroic mirror disposed within the housing. Yet further included is analyzing the short wave infrared light with an one-dimensional (1D) camera pixel array disposed within the housing.

In addition to one or more of the features described above, or as an alternative, further embodiments may include that a plurality of images captured with the 1D camera determines a quantity of a gas present in an environment surrounding the housing based on an amount of absorption of the laser light emitted from the housing.

In addition to one or more of the features described above, or as an alternative, further embodiments may include that the gas comprises carbon monoxide or methane.

Further disclosed is a method for determining gas quantification and localization. The method includes emitting and receiving infrared light with a hazardous gas detector. Also included is analyzing a short wave infrared light portion of the received infrared light with a one-dimensional (1D) camera pixel array disposed within a housing of the gas detector. Further included is analyzing a long wave infrared light portion of the received infrared light with a two-dimensional (2D) camera pixel array disposed within the housing. Yet further included is evaluating the analyzed information between sensors to determine a presence of a gas.

In addition to one or more of the features described above, or as an alternative, further embodiments may include that a plurality of images captured with the 1D camera and the 2D camera determines a quantity of a gas present in an environment surrounding the housing based on an amount of absorption of the laser light emitted from the housing.

In addition to one or more of the features described above, or as an alternative, further embodiments may include that the gas comprises carbon monoxide or methane.

In addition to one or more of the features described above, or as an alternative, further embodiments may include that the hazardous gas detector is scanned using gimbals to determine the presence of gas in the environment.

BRIEF DESCRIPTION OF THE DRAWINGS

The present disclosure is illustrated by way of example and not limited in the accompanying figures in which like reference numerals indicate similar elements.

FIG. 1 is a perspective view of a hazardous gas detector;

FIG. 4 is a schematic view of the hazardous gas detector;

FIG. 5 is a view of laser light paths within the hazardous gas detector; and FIG. 6 is a perspective view of the hazardous gas detector coupled to an aircraft according to an aspect of the disclosure.

DETAILED DESCRIPTION

Figure 3:
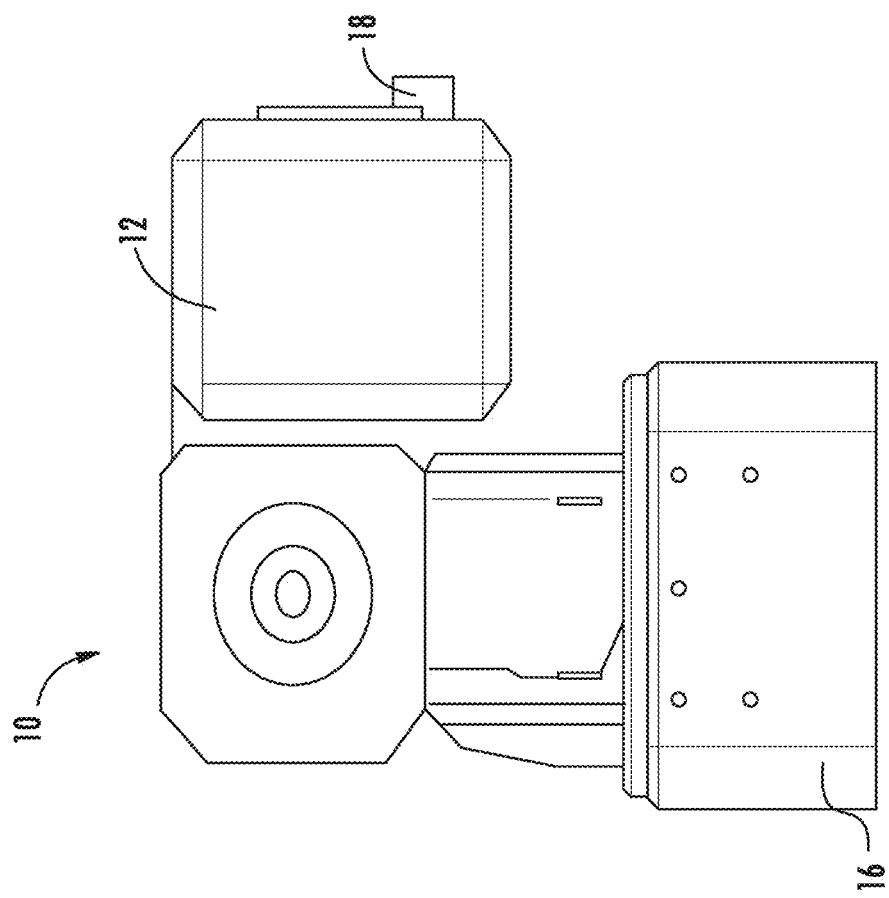
FIG. 3 is an elevational view of the hazardous gas detector.
Figure 2:
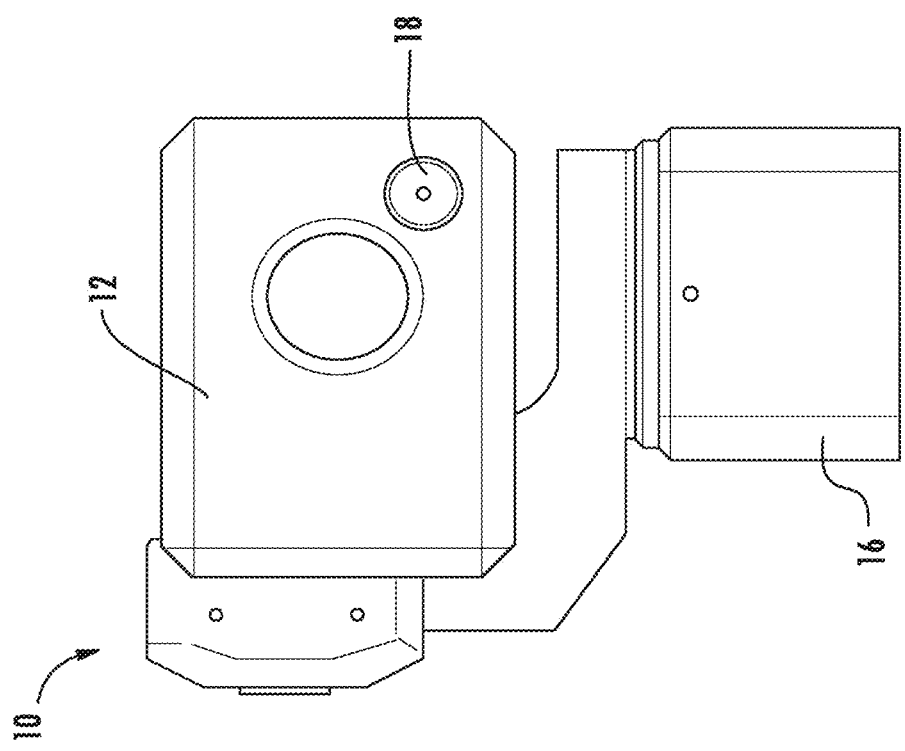
FIG. 2 is an elevational view of the hazardous gas detector.

FIGS. 1-3 illustrate a hazardous gas detector that is generally referenced with numeral 10. The gas detector 10 includes a housing 12 that defines an interior region 14 of the gas detector 10. The housing 12 is operatively coupled to a structure 16 that facilitates movement of the housing 12. In the illustrated embodiment, the structure is a gimbal mount that facilitates movement of the housing in two directions to scan an environment surrounding the housing 12. As will be appreciated from the description herein, scanning the surrounding environment allows the gas detector 10 to analyze the environment for certain gases of interest.

Referring now to FIGS. 1-5, coupled to the housing 12 is a laser emitting component 18 that is configured to emit a laser light 20 that extends away from the housing 12. The laser light 20 is then reflected back to the housing 12. As will be appreciated from the description herein, the laser light 20 is analyzed with a plurality of optical components located within the housing 12 to determine gas quantification and spatial information related to a gas present in the surrounding environment. One advantage of optical-based gauges is that they can perform non-contact, stand-off or remote sensing distance spectroscopy of various materials. For remote sensing particularly, it may be necessary to operate in atmospheric transmission windows. For example, two windows in the short wave infrared (SWIR) that transmit through the atmosphere are approximately 1.4-1.8 microns and 2-2.5 microns, but it is to be appreciated that the term SWIR, as used herein, may refer to any wavelength within the near-infrared region of the electromagnetic spectrum, which covers between approximately 0.7 microns (700 nm) to about 2.5 microns (2500 nm).

The SWIR wavelength range may be particularly valuable for identifying materials based on their chemical composition because the wavelength range comprises overtones for numerous chemical compounds. Thus, mixtures of gases, liquids and solids that comprise these chemical compounds may exhibit characteristic spectral features in the SWIR wavelength range. For example, methane and carbon monoxide may be two gases of interest that exhibit such features in the SWIR wavelength.

As shown in FIG. 6, the gas detector 10 may be coupled to an aircraft 21 in some embodiments. Such an embodiment is useful for remote sensing of natural gas. The laser emitting component 18 may direct the laser light 20 toward the ground, and the reflected light may then be measured using the optical components of the gas detector 10, as described herein. Thus, the aircraft may be sampling a volume of interest (VOI) to look for natural gas. In yet another embodiment, for example, the materials of interest could be aerosols of various sorts. Regardless of the material of interest, the gas detector 10 projects a certain intensity of laser light 20 through a gas cloud and checks for this light intensity reduction. The use of an aircraft is one particular example of a remote sensing system, but other system configurations may also be used and are included in the scope of this disclosure. For example, the gas detector 10 may be placed in a fixed location. In yet another embodiment, the gas detector 10 could be placed on a ground vehicle such as an automobile or a truck. If the gas detector 10 is compact and lightweight, it could be carried by a person in the field, either in their hands or in a backpack.

Referring now to FIGS. 4 and 5, returning light 22 that includes the laser light 20 and any additional ambient light, such as sunlight, is received by the gas detector 10. In particular, the returning light 22 is passed through a lens 24 that is disposed within an aperture 26 (FIG. 1) defined by the housing 12. The lens 24 rejects visible light 28 from the returning light 22 and allows penetration of infrared light 30 into the interior region 14 of the gas detector 10. The infrared light 30 is projected onto a mirror 32 that separates a short wave portion of the light, which is referred to herein as the SWIR 34, from a long wave portion 36; so called long wave infrared (LWIR). In some embodiments, the mirror 32 is a dichroic mirror.

The long wave portion 36 is filtered sunlight that is directed toward a two-dimensional (2D) camera 38 disposed within the interior region 14 of the housing 12. In some embodiments, the 2D camera 38 is a 2D long wave infrared (LWIR) focal plane array (FPA). The 2D camera 38 captures thermal images of the VOI.

The short wave portion of the light 34 is redirected toward one or more optical notch filters 42 disposed within the interior region 14 of the housing 12. After passing through the notch filters 42, a filtered light 44 is directed toward a one-dimensional (1D) camera 46—a line scan camera. The 1D camera 46 is a pixel array in which the pixels are in a single row. The number of pixels in the 1D pixel array ranges from 128 to 1028. In some embodiments, the 1D camera is a 2D SWIR focal plane array (FPA).

As discussed above, an aircraft with the gas detector 10 may provide aerial localization and quantification of leaks. By way of non-limiting example, the aircraft may fly at about 100 m elevation and about 50 m/s velocity while interrogating a region with a laser. At a first approximation, the ground surface will reflect light as a Lambertian surface with about 5%-15% reflectivity. However, the return intensity varies due to non-Lambertian reflectivity, e.g., from man-made structures and environmental features. As the aircraft traverses an area, the gimbal 16 provides aircraft movement compensation (to allow signal integration, e.g., for 0.1 s) and aides in reducing ground effects by providing different camera-to-ground pose while the system scans for optical signatures of methane.

In the SWIR band, sunlight and spectrally tuned laser energy will pass through a gas plume (e.g., methane) and are both selectively absorbed and reflected off the ground. Utilizing a 256 pixel linear focal plane array sensitive to the SWIR band and a 7 degree field of view, a 25 m swath on the surface is imaged by passive illumination. The passively illuminated SWIR data is analyzed to provide localization of the leak and increase fidelity by identifying spatiotemporal features of the plume. Simultaneously, a laser illuminates a subset of pixels (as described below) to provide local plume concentrations. The utilization of a synchronizing controller to tag laser information to the image data enables an increase in sensitivity enabled by differential spectroscopy and adaptive imaging dwell time. The controller enables collimated light from the laser to be modulated between 2.315 μm and 2.317 μm, which enables interrogation of methane off and on the resonant absorption peak centered at 2.317 μm. Actively illuminated pixels at 2.315 μm and 2.317 μm are compared and the difference in intensity determines the gas concentration along the path length given the aircraft altitude and pose. The active illumination of a few pixels provides point quantification of the gas plume. The combination of active and passive illumination of the plume provides spatiotemporal features and localized quantification. The tagged data set is then passed to algorithms for analysis to determine leak detection, location and quantification.

The data acquisition, data tagging, and management is supervised by a camera controller to ensure system accuracy and precision. Harnessing control methodologies, laser source data, 1D SWIR camera data, and 2D LWIR camera data is tagged for analysis. This data acquisition and control methodology enables the VOI to be analyzed and then compared to the 2D LWIR (confirmer) data and associated ground data for efficacy and accuracy.

The laser power and speed requirements require a driving power of 110 mW during pulsed operation. The laser temperature may be controlled via thermo-electric driver to provide 2 nm wavelength tuning, which requires ±10° C. temperature control at 0.1° C. resolution in some embodiments. This provides wavelength stability of +/−0.2 nm at 2.315 μm. The laser wavelength scanning from 2.315 μm to 2.317 μm wavelengths can be accomplished by temperature modulation at the thermo-electric driver. However, this approach is limited to a maximum of approximately 10 Hz in some embodiments. The scanning speed of the current system requires switching wavelengths at a rate of 150-200 Hz in some embodiments. The faster wavelength modulation can be achieved by locally heating the active element in the laser. This is accomplished by holding the laser temperature constant with the thermo-electric cooler and providing current pulses to locally heat the active element. Utilizing the camera controller, a programmed current pulse train is generated to modulate the switch wavelengths. The laser control is also synchronized to the camera control. The read/write function of the camera is triggered by a signal to capture frames. The camera controller data and 1D SWIR camera data is then sent to an embedded data acquisition system. In the embedded data acquisition system, the camera controller data, flight record data, 1D SWIR camera, and 2D LWIR camera data are tagged. The tagged data is then stored for analysis by the algorithms.

In some embodiments, detection is based on methane gas absorbing light through its molecules vibrational modes. Of interest in such embodiments is the absorption of light by methane at 2.317 μm. The absorption coefficient of methane is $2 \times 10^{-5}$ L/g/m at 25° C. and 1 atm. In contrast, a shift in wavelength of 2 nm to 2.315 μm results in essentially no light absorption by methane. Utilizing this property of methane, the embodiment of the laser light may emit collimated (<0.01 rad) laser light tunable between 2.317 μm and 2.315 μm with an average power of 7 mW. The low power of the laser enables eye safe operation at any distance.

Because the 1D camera 46 is a one-dimensional array of pixels, the field of view of the 1D camera 46 is narrow in one direction and wide in the other. The laser in the form of the filtered light 44 that is directed toward the 1D camera 46 provides active illumination on only a few of the pixels, with the illuminated pixels forming an illuminated portion of the pixel array. The line array will image both the actively illuminated region and passively illuminated regions to the sides of the actively illuminated region. Each image frame is stitched together to form a 2D image where one dimension is spatial and the other is temporal. This provides both quantification of the gas within the active area and spatio-temporal features within the passively illuminated areas.

The gas detector 10 may be used with a mobile observing platform, e.g., an unmanned aerial system (UAS), with low-cost, lightweight portable sensing package. It comprises a laser source illuminating the scene, whose backscatter radiation is captured through a 1D linear array and a 2D focal plane array. The single laser source, in the limit, turns this sensing system into a point sensor at 100 m range. However, exploration of the mutual information between the 1D and 2D sensor may be performed, and between the illuminated and un-illuminated parts of the sensing array elements to improve measurements and uncertainty quantification in contrast to purely differential absorption measurement in a Gaussian neighborhood of a pixel. The UAS sensor package also includes in-situ sensors for measurement of meteorological variables.

Primary data is gathered by systematically traversing the domain in an Eulerian fashion, and transects are used to constrain a numerical model. The model's predictions and associated uncertainties trigger additional locations and modalities for localization, source estimation, and uncertainty reduction. For example, locations could include boundary scans for winds, sampling at locations hypothesized as sources, and reducing concentration uncertainties upwind. In this way, over time, the domain is intelligently sampled to include systematic and adaptive components to produce a clear picture. The remote IR sensors may be dynamically calibrated for sensitivity and range using vertically integrated in-situ measurements by the mobile sensor. The flight paths for this are also included in the adaptive sampling part of the observation.

In some embodiments, if a gas plume is detected by the linear array, an alarm will trigger. Continuous scanning of the area may provide a real time status of the plume to a person or a control room.

The embodiments of the gas detector 10 disclosed herein can be tuned to provide single hazardous gas species detection or multiple gas species detection on the same system. The embodiments described herein overcome barriers of prior designs by utilizing a combination of SWIR 1D arrays and active illumination via a laser. It is contemplated that the apparatus and method described herein can provide 1 ppm or lower sensitivity at close range and 2.5% sensitivity with coverage over 100 meters.

Embodiments may be implemented using one or more technologies. In some embodiments, an apparatus or system may include one or more processors and memory storing instructions that, when executed by the one or more processors, cause the apparatus or system to perform one or more methodological acts as described herein. Various mechanical components known to those of skill in the art may be used in some embodiments.

Embodiments may be implemented as one or more apparatuses, systems, and/or methods. In some embodiments, instructions may be stored on one or more computer program products or computer-readable media, such as a transitory and/or non-transitory computer-readable medium. The instructions, when executed, may cause an entity (e.g., a processor, apparatus or system) to perform one or more methodological acts as described herein.

While the disclosure has been described in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the scope of the disclosure. Additionally, while various embodiments have been described, it is to be understood that aspects of the disclosure may include only some of the described embodiments. Accordingly, the disclosure is not to be seen as limited by the foregoing description, but is only limited by the scope of the appended claims.

What is claimed is:

1. A hazardous gas detector comprising:
a housing defining an interior region;
a laser emitting component oriented to emit a laser light away from the housing;
a lens disposed within an aperture defined by the housing, the lens allowing returning infrared light of the laser light to enter the interior region;
a mirror disposed within the interior region and oriented to split the returning laser light into a short wave infrared light and a long wave infrared light; and
a one-dimensional (1D) camera pixel array disposed within the interior region, the 1D camera imaging a planar region that includes an illuminated portion comprising the short wave infrared light.

2. The hazardous gas detector of claim 1, wherein a plurality of images captured with the 1D camera determines a quantity of a gas present in an environment surrounding the housing based on an amount of absorption of the laser light emitted from the housing.

3. The hazardous gas detector of claim 2, wherein the gas comprises carbon monoxide or methane.

4. The hazardous gas detector of claim 1, further comprising at least one optical notch filter disposed within the housing and between the mirror and the 1D camera pixel array.

5. The hazardous gas detector of claim 1, wherein the 1D camera pixel array is a 1D short wave infrared focal plane array.

6. The hazardous gas detector of claim 1, wherein the 1D camera pixel array comprises a number of pixels ranging from 128 to 1028.

7. The hazardous gas detector of claim 1, further comprising a two-dimensional (2D) camera disposed within the housing for imaging of the long wave infrared light.

8. The hazardous gas detector of claim 7, wherein the 2D camera is a 2D long wave infrared focal plane array.

9. The hazardous gas detector of claim 7, wherein the 2D camera provides an image for visual inspection by a user.

10. The hazardous gas detector of claim 1, wherein the mirror is a dichroic mirror.

11. The hazardous gas detector of claim 1, wherein the housing is operatively coupled to a gimbal mount to allow movement of the housing.

12. A method of detecting hazardous gas comprising:
emitting a laser light from a housing;
receiving an infrared light portion of the laser light through a lens disposed within an aperture defined by the housing;
separating a short wave infrared light from the infrared light portion with a dichroic mirror disposed within the housing; and
analyzing the short wave infrared light with an one-dimensional (1D) camera pixel array disposed within the housing.

13. The method of claim 12, wherein a plurality of images captured with the 1D camera determines a quantity of a gas present in an environment surrounding the housing based on an amount of absorption of the laser light emitted from the housing.

14. The method of claim 12, wherein the gas comprises carbon monoxide or methane.

15. A method for determining gas quantification and localization comprising:
emitting and receiving infrared light with a hazardous gas detector;
analyzing a short wave infrared light portion of the received infrared light with a one-dimensional (1D) camera pixel array disposed within a housing of the gas detector;
analyzing a long wave infrared light portion of the received infrared light with a two-dimensional (2D) camera pixel array disposed within the housing; and
evaluating the analyzed information between sensors to determine a presence of a gas.

16. The method of claim 15, wherein a plurality of images captured with the 1D camera and the 2D camera determines a quantity of a gas present in an environment surrounding the housing based on an amount of absorption of the laser light emitted from the housing.

17. The method of claim 15, wherein the gas comprises carbon monoxide or methane.

18. The method of claim 15, wherein the hazardous gas detector is scanned using gimbals to determine the presence of gas in the environment.

* * * * *